United States Patent [19]

Segall et al.

[11] Patent Number: 5,574,019

[45] Date of Patent: Nov. 12, 1996

[54] METHOD OF PERFUSING A PRIMATE

[75] Inventors: Paul E. Segall; Hal Sternberg; Harold D. Waitz, all of Berkeley, Calif.

[73] Assignee: Biotime, Inc., Berkeley, Calif.

[21] Appl. No.: 119,962

[22] Filed: Sep. 10, 1993

Related U.S. Application Data

[63] Continuation of Ser. No. 860,703, Apr. 1, 1992, abandoned, which is a continuation-in-part of Ser. No. 687,841, Apr. 19, 1991, abandoned.

[51] Int. Cl.$^6$ .......................... A01N 43/04; A01N 25/00; A61M 37/00; A61M 5/00
[52] U.S. Cl. .................. 514/23; 514/58; 514/54; 514/53; 514/59; 514/777; 514/832; 514/833; 435/2; 604/48; 604/49; 604/4; 604/5; 604/6; 604/7
[58] Field of Search .................. 514/23, 56, 59, 514/60, 54, 53, 58, 777, 832, 833; 435/1, 2; 604/4, 5, 6, 7, 49, 48

[56] References Cited

U.S. PATENT DOCUMENTS

| | | | |
|---|---|---|---|
| 4,245,121 | 1/1981 | Wissner et al. | 560/118 |
| 4,923,442 | 5/1990 | Segall et al. | 514/23 |
| 4,927,806 | 5/1990 | Kramer et al. | 514/2 |
| 5,082,831 | 1/1992 | Leaf et al. | 435/1 |
| 5,084,558 | 1/1992 | Rowan | 435/1 |
| 5,130,230 | 7/1992 | Segall et al. | 435/1 |

*Primary Examiner*—John Kight
*Assistant Examiner*—Louise N. Leary
*Attorney, Agent, or Firm*—Karl Bozicevic; Fish & Richardson P.C.

[57] ABSTRACT

The present invention relates to the field of compositions of matter, disclosing compositions of matter which as aqueous solutions, may be used to perfuse a living or non-living subject in need of perfusion. The solutions according to the invention are typified by an aqueous solution comprising a polysaccharide oncotic agent, a physiologically compatible buffer, a simple hexose sugar, dissolved chloride salts of calcium, sodium and magnesium, and a dissolved organic salt of sodium. The solutions according to the invention are effective substitutes for blood. In addition the solution according to the invention may be used to preserve the biological integrity of the organs of a mammalian donor organism as shown by superior anatomical integrity of cryopreserved organs and tissues of subjects perfused with the solution of the invention. The solutions may be used for a number of purposes including maintaining a partially or substantially completely exsanguinated subject at temperatures substantially below those normally maintained by a mammal. The solutions may be used in conjunction with hyperbaric environments to maintain such partially or completed exsanguinated subjects alive without infusing blood back into the subject. Methods for using the solutions for these purposes are disclosed.

33 Claims, No Drawings

METHOD OF PERFUSING A PRIMATE

This patent application is a continuation of application Ser. No. 07/860,703 filed on Apr. 1, 1992 now abandoned which is a continuation-in-part application of U.S. patent application Ser. No. 07/687,841, filed Apr. 19, 1991 now abandoned.

FIELD OF THE INVENTION

The present invention relates to the field of compositions of matter which as aqueous solutions, may be used to perfuse a living subject in need of perfusion. The solutions according to the invention are effective substitutes for blood. In addition the solution according to the invention may be used to preserve the biological integrity of the organs of a mammalian donor organism as shown by superior anatomical integrity of cryopreserved organs and tissues of subjects perfused with the solution of the invention. The solutions may be used for a number of purposes including maintaining a partially or substantially completely exsanguinated subject at temperatures substantially below those normally maintained by a mammal.

BACKGROUND OF THE INVENTION

Perfusion solutions and blood substitutes are known. The blood substitutes of Collins et al, Kidney preservation for transplantation. Lancet 1219–1222 (1969); Collins G. M., Hypothermic kidney storage. Transplant. Proc. IX:1529 (1977); Fischer et al, Flush solution 2, a new concept for one to three day hypothermic renal storage preservation. Transplantation 39:2, 122–126 (1985); Ross et al, 72-hour canine kidney preservation without continuous perfusion. Transplantation 21:498 (1976); Sacks et al, Transplantation 19:283 (1974) and Kallerhoff et al, Effects of the preservation conditions and temperature on tissue acidification in canine kidneys. Transplantation 39:5, 485–489 (1985) all consist only of low molecular weight molecules that readily traverse the capillary bed of the subject and thus are generally incapable of maintaining proper ionic or fluid balance or plasma volume when used in an intact mammalian subject.

Klebanoff and Phillips, Cryobiology 6:121–125 (1969) disclosed hypothermic asanguinous perfusion of dogs with 11 of 15 subjects surviving up to 95 minutes when perfused with buffered Ringer's lactate at 7.1 to 16 degrees C. (44.6–60.4 degrees F.).

Those blood substitutes that have an impermeable substance to maintain volume use human serum albumin or a mixture of plasma proteins, as the impermeate molecule to maintain blood volume. These are disclosed in Wall et al., Simple hypothermic preservation for transporting human livers long distances for transplantation, Transplantation, 23:210 (1977); Belzer et al., Combination perfusion-cold storage for optimum cadaver kidney function and utilization, Transplantation 39:2, 118–121, (1985).

Haff et al., Journal of Surgical Research 19:1, 13–19 (1975) describe the asanguineous hypothermic perfusion of dogs using two solutions: the first, a flush solution comprised of pooled delipidated homologous plasma and electrolytes, and the second comprised of pooled delipidated homologous plasma, electrolytes and additional potassium chloride at a concentration of 10 mEq/liter. Haff et al also disclose the use of a pulsatile pump oxygenator and hypothermic perfusion with their solutions and suggest that the procedures could be used for long distance transport of cadaver organ donors and as an alternative to hypothermic circulatory arrest for blood-free intricate surgery.

Non plasma-based solutions for organ preservation are disclosed in Bishop et al., Evaluation of hypertonic citrate flushing solution for kidney preservation using the isolated perfused rat kidney. Transplantation 25:5, 235–239 (1978). This article discloses a perfusion solution that included 50 g/liter dextran 40, a concentration that differs markedly from those of the solutions of the present invention. In addition, the electrolyte and ion concentrations differ markedly from those disclosed for the present invention.

Segall et al., Federation Proceedings 44(3):623, (1985) disclose that a Ringer's lactate-based heparinized blood substitute containing 6% dextran 40 was used to lower the body temperature of hamsters prior to the circulation of cold-protective solutions, which are not disclosed, for 1 to 1.5 hours.

Segall et al., (1987) Federation Proceedings, page 1338, disclose that a blood substitute, which included dextrose (180 mg/dl) and 25 mM HEPES, was used to perfuse a dog to 3 degrees C. when perfusion was stopped entirely. There is no disclosure of the complete composition of the blood substitute.

Segall et al, U.S. Pat. No. 4,923,442 disclose a number of solutions used in blood substitution of living subjects all of which include at least some concentration of a cardioplegic agent, usually potassium ion. Segall et al., U.S. Pat. No. 4,923,442 also discloses surgical methods, particularly in respect to instrument placement and the control of pulmonary wedge pressure generally applicable to perfusion of subjects. U.S. Pat. No. 4,923,442 is incorporated herein by reference.

DESCRIPTION OF THE INVENTION

The present invention comprises a mixture of materials including essential electrolytes, an oncotic agent, simple sugar, and a physiologically compatible buffer. As an aqueous solution the osmolality of the solution approximates that of plasma.

The solution according to the invention may be used for a number of purposes including maintaining a partially or substantially completely exsanguinated subject alive at temperatures substantially below those normally maintained by a mammal. In addition the solutions may be used to maintain a partially or substantially completely exsanguinated subject alive at normal body temperatures. Furthermore, with the addition of certain adducts, the solution may be used to maintain the life or biological integrity of a perfused subject and its organs during and after exposure to profound hypothermic conditions.

The solution can also be used to maintain a euthermic subject in a pressurized environment with increased oxygen concentration up to 100% $O_2$ for time periods sufficient to permit adequate restoration of blood components.

The solution according to the invention may be used to perfuse and chill a mammalian subject to temperatures profoundly hypothermic to the subject's normal temperature. The solution can be used to maintain the subject in profound hypothermia for long periods of time, usually exceeding an hour, from which an intact subject can recover without apparent durable ill effects.

An important distinction of the present invention over that of the prior art Segall et al U.S. Pat. No. 4,929,442 is that the solution according to the invention does not require multiple solutions for it to be effectively administered to a subject for the purposes of blood substitution, or low temperature maintenance of a mammalian subject.

In addition the present solutions of the invention do not require the presence of a cardioplegia agent in any of the solutions, whereas a cardioplegia agent is part of the base solution and all of the other solutions disclosed and claimed in U.S. Pat. No. 4,924,442. The absence of the cardioplegia agent, and in particular the lack of potassium chloride or potassium ion as a requirement in the solution according to the invention makes the solution of the present invention convenient to administer to a variety of mammalian subjects and for a variety of purposes.

Importantly, the solution according to the invention may be used to fully blood substitute a mammalian subject without the use of potassium ion in the solution at all. The omission of potassium salt or ion from the solution allows the solution to be used in mammalian subject during all phases of blood substitution from initial washout of the subject's blood through full substitution of all or substantially all circulating blood with maintenance of the subject in a blood less state and finally during the phase of re-perfusion with blood.

This is particularly advantageous when the solution according to the invention is administered to primate subjects. Primate red blood cells contain high concentrations of potassium ion. When primate blood is stored, for any length of time, as is the case with virtually all blood obtained from blood banks, even low levels of lysis of the red blood cells practically always results in high potassium ion concentrations due to release of potassium ion from the lysed primate red blood cells. As a result this blood is hyperkalemic when infused. This is no problem if blood is infused into patients with sufficent circulating blood since the high potassium ion concentration is diluted. By contrast, if primate blood is transfused into the maintenance solution described in U.S. Pat. No. 4,924,442, which contains high concentrations of potassium, the potassium ion in the transfused blood cannot dilute to safe levels in a higher volume of circulating blood having normal potassium concentration and cardiac insufficiency may and frequently does occur.

By contrast, the solution according to the present invention contains no potassium and therefore it allows dilution of the potassium ion in stored transfused blood into the larger reserve of the blood substitute solution. As a result high concentrations of potassium ion and potential cardiac arrhythmias and cardiac insufficiency caused thereby can be more easily controlled using the solutions according to the present invention.

In greater detail, the present invention comprises a mixture of materials which when placed in aqueous solution may be used to perfuse a subject in need thereof. The materials may be provided as a dry sterile mixture to which sterile water or sterile saline solution may be added to form an aqueous solution. If provided as a dry sterile mixture, the materials may be provided in a sterile container suitable for mixture with sterile water or sterile saline. Alternatively the mixture of materials may be provided in a sterile container as an aqueous solution.

The mixture of materials according to the invention comprises an oncotic agent, a physiologically compatible buffer, a simple hexose sugar, chloride salts of calcium, sodium and magnesium, and an organic salt of sodium. If the mixture is provided as a dry sterile mixture suitable for addition by sterile saline solution, the amount of chloride salt of sodium in the dry mix is adjusted or omitted in amount equal to the sodium chloride contained in the sterile saline solution used. If the mixture is provided as an aqueous solution the mixture comprises water, an oncotic agent, a physiologically compatible buffer, a simple hexose sugar, dissolved chloride salts of calcium, sodium and magnesium, and a dissolved organic salt of sodium. If the mixture according to the invention is provided as an aqueous solution, it is preferable to provide the solution as a sterile solution in a sterile container. Alternatively, the aqueous solution according to the invention may be provided as a non-sterile solution and may be subsequently sterile filtered into or autoclaved in sterile containers.

For purposes of the further description of the invention, the mixture according to the invention will be discussed as an aqueous solution. From the following description of the invention it is expected that one ordinarily skilled in the art would be enabled to provide the mixture as a dry mixture and make the adjustments to amounts of sodium chloride and organic salt of sodium as necessary to accommodate the amounts of sodium chloride found in normal saline solution, which may be used as a diluent for the dry mixture according to the invention.

A number of organic salts of sodium may be used in the mixture according to the invention. Such organic salts include sodium citrate, sodium gluconate, sodium pyruvate, sodium succinate, sodium bicarbonate and sodium lactate. In the preferred embodiment of the invention, sodium gluconate is used. The use of sodium citrate is also desirable in the solutions according to the invention. In general, although acceptable in the solution according to the invention, the pyruvate, lactate and bicarbonate salts of sodium may be less desirable. The build up of pyruvate and lactate may have undesirable physiological effects on an animal subject including causing muscle cramping. Sodium bicarbonate may change the buffering capacity of the solution according to the invention.

The amount to the organic salt of sodium used is calculated to supplement the concentration of sodium ion obtained in the solution from sodium chloride so that the concentration of sodium ion obtained from the organic salt of sodium is sufficient to bring the concentration of sodium ion in the solution to a concentration about that of physiologically normal plasma without providing additional chloride ion. Therefore, when taking into account the amount or concentration of sodium ion obtained from the organic salt of sodium and sodium chloride, the concentration of sodium ion in the solution is about the concentration of sodium ion found in physiologically normal plasma.

Thus for example, when sodium gluconate is used, the concentration of the of sodium gluconate is sufficient when taken together with the sodium chloride in solution, to bring the concentration of sodium ion in the solution to a concentration about that of physiologically normal plasma. In terms of molar concentration, the concentration of the organic salt of sodium in the solution is in a range of about 5 mM to 70 mM. Preferably the concentration of the organic salt of sodium is about 27 mM. When sodium gluconate is used it will be used within the foregoing concentration range and preferred concentration.

The solution according to the invention also includes a concentration of calcium, sodium and magnesium ion which is within the range of normal physiological concentrations of said ions in plasma. The solution according to the invention does not include potassium ion. In general the desired concentration of these ions is obtained from the dissolved chloride salts of calcium, sodium and magnesium and in the case of sodium from a dissolved organic salt of sodium which is also in solution.

In the solution according to the invention the sodium chloride concentration is in a range from 70 mM to about 160 mM. Preferably the concentration of sodium chloride in the solution according to the invention is in a range of about 85 to 95 mM. In the most preferred embodiment of the invention the concentration of sodium chloride is about 90 mM.

Also in the solution according to the invention the concentration of calcium chloride is in a range of about 0.5 mM to 4.0 mM. Preferably the concentration of calcium chloride in the solution according to the invention is in a range of about 1.5 mM to 3.5 mM. More preferably the concentration of calcium chloride is in a range of about 1.5 mM to 2.5 mM. In the most preferred embodiment of the invention the concentration of calcium chloride is about 2 mM.

Further in the solution according to the invention, the concentration of magnesium chloride is in a range of 0 to 10 mM. It is preferred to include at least a small amount of magnesium chloride in the solution in a range of about 0.5 mM to 10 mM. Most preferred, the solution according to the invention has a magnesium chloride concentration of about 2 mM. It important not to include excessive amounts of magnesium ion in the solution according to the inventions-because high magnesium ion concentrations negatively affect the strength of cardiac contractile activity.

Also included in the solution according to the invention is an amount of simple hexose sugar. Such sugars are exemplified by glucose, fructose and galactose. While non-nutritive hexose sugars such as sorbitol and xylitol could be used in the solution, they are not preferred. In the preferred embodiment of the invention nutritive hexose sugars are used. A mixture of the sugars could be used in the solutions according to the invention. Most preferred in the solution according to the invention is glucose. In general the concentration of sugar in the solution according to the invention will be in a range between 2 mM and 10mM. A concentration of 5 mM is preferred with respect to glucose. It may however be desirable to increase the concentration of hexose sugar to lower fluid retention in the tissues of a subject. Thus the range of hexose sugar may be expanded up to about 50 mM if necessary to prevent or limit edema in the subject under treatment.

The pH of the solution according to the invention is maintained by the use of a physiologically compatible buffer. By physiologically compatible buffers is meant buffers that buffer in the range of physiological pH between about 7.2 and 7.9. Such buffers may have a wider range. In general the physiologically compatible buffer in the solution according to the invention will have has a pKa of 7.77 at 37° C. and a delta pKa/0° C. of −0.031.

In addition such buffers will be non-toxic to living subjects. In particular tris[Hydroxylmethyl]methylaminomethane (TRIS) is generally regarded as safe for use in animals and human beings. Other buffers suitable for use in the blood substitute according to the invention include: N-2-Hydroxyethylpiperazine-N'-2-hydroxypropanesulfonic acid (HEPES) buffer useful pH range between 6.8 and 8.2.; 3-(N-Morpholino) propanesulfonic acid (MOPS) pH range 6.5–7.9; 2-([2-Hydroxy-1,1-bis(hydroxymethyl)ethyl] amino) ethanesulfonic acid (TES) pH range 6.8–8.2, 3-[N-tris(Hydroxy-methyl) methylamino]-2-hydroxypropanesulfonic acid (TAPSO) pH range 7.2–8.2 and 4-[2-hydroxyethly]-1-piperazinepropanesulfonic acid (EPPS) pH range 7.3–8.7. In the present invention TRIS is preferred.

The concentration of TRIS base used in the solution to achieve the desired buffering capacity is about 25 mM. When making the solution according to the invention, the pH of the solution is brought to about 7.8 by addition of hydrochloric acid at about 25° C.

By oncotic agent is meant molecules whose size is sufficient to prevent their loss from the circulation by traversing the fenestrations of the capillary bed into the interstitial spaces of the tissues of the body. As a group, oncotic agents are exemplified by blood plasma expanders.

Human serum albumin is a blood plasma protein used to expand plasma volume. Also known are polysaccharides, generally characterized as glucan polymers which are used as blood plasma expanders. In general, it is preferred that the polysaccharide is one that is non-antigenic.

Hetastarch (American Home Products) is an artificial colloid derived from a waxy starch composed almost entirely of amylopectin with hydroxyethyl ether groups introduced into the alpha (1 . . . 4) linked glucose units. The colloid properties of a 6% solution (wt/wt) of Hetastarch approximates that of human serum albumin. Other polysaccharide derivatives may be suitable as oncotic agents in the solutions according to the invention including hydroxymethyl alpha (1 . . . 4) or (1 . . . 6) polymers. Cyclodextrins may be suitable as oncotic agents in the blood substitute according to the invention.

D-glucose polymers are preferred. Dextran, which is D-glucose linked predominantly in alpha (1 . . . 6) linkage, is especially preferred. Polysaccharides such as dextran in a molecular weight range of 30,000 to 50,000 daltons (D) are preferred. Most preferred is Dextran 40 having a molecular weight of about 40,000 D.

High molecular weight polysaccharides, such as Dextran 70, having a molecular weight of about 70,000 D are generally less preferred because they increase viscosity of the colloidal solution and impair the achievement of high flow rates. Such high molecular weight dextran solutions, however may be more effective in preventing tissue swelling due to their lower rates of leakage from capillaries, and may be particularly useful in the treatment of cerebral ischemia at hyperbaric oxygen tensions while at the same time effectively managing cerebral oedema. In such circumstances, it may be desirable to use higher molecular weight polysaccharide such as dextran in a molecular weight range of 50,000 to 70,000 D.

When Dextran 40 is used in the solutions according to the invention about 8% Dextran 40 (wt/wt) or about 80 grams (g) per liter (1) of water is used. Molarity of the blood substitute according to the invention will be in a range of about 290 to 330 milliMolar with an molarity of about 300 being preferred. Most preferred is a final molarity of about 298 mM.

The concentration of the polysaccharide in the solutions according to the invention is sufficient to achieve, when taken together with chloride salts of sodium, calcium and magnesium, organic ion from the organic salt of sodium and hexose sugar discussed herein above colloid osmotic pressure approximating that of normal human serum, about 28 mm Hg.

The solution according to the invention may be used as a circulating solution in conjunciton with oxygen or hyperbaric oxygen at normal body temperatures, or with or without hyperbaric oxygen in subjects during procedures. The solution according to the invention may also be used as a circulating solution in subjects during procedures when the subject's body temperature is reduced significantly below the subjects normal temperature. When warm-blooded subjects are exposed to low temperature conditions during surgical procedures and in cadaver organ donation at low temperature, it is generally desirable to replace the subject's blood with a cold circulating solution according to the invention, designed to perfuse and maintain the subject and its organs intact during the procedure.

The solution of the present invention may be administered intravenously or intraarterially to a euthermic subject which is placed in a pressurized atmosphere of increased oxygen concentration up to 100% oxygen or to such a subject undergoing a procedure during which the subject's body temperature is reduced significantly below the subjects normal temperature whether or not hyperbaric oxygen is used. While the solution is being administered to and circulated through the subject, various agents such as cardioplegic agents may be administered either directly into the subjects circulatory system, administered directly to the subject's myocardium, or added to the circulating solution according to the invention to achieve desired physiological effects such as maintaining regular cardiac contractile activity, stopping cardiac fibrillation or completely inhibiting contractile activity of the myocardium or heart muscle.

By cardioplegic agent is meant materials that cause myocardial contraction to cease. Cardioplegic agents include certain anesthetic such as lidocaine, procaine and novocaine and monovalent cations such as potassium ion in concentrations sufficient to achieve myocardial contractile inhibition. Concentrations of potassium ion sufficient to achieve this effect are generally in excess of 15 mM.

During revival of a subject after a period of subnormal temperature or cryonic maintenance using the solution according to the invention to maintain the subject, the subject may be reinfused with a mixture of the solution according to the invention and blood retained from the subject or obtained from blood donors. As the subject is warmed whole blood is infused until the subject achieves an acceptable hematocrit, generally exceeding hematocrits of about 30% When an acceptable hematocrit is achieved perfusion is discontinued and the subject is revived after closure of surgical wounds using conventional procedures In general, the solution according to the invention is administered by intravenous line when the subject is at normal temperature or to a chilled subject using a pumped circulating device such as a cemtrifugal pump, roller pump, peristaltic pump or other known and available circulatory pump. The circulating device is connected to the subject via cannulae inserted surgically into appropriate veins and arteries. When the solution is administered to a chilled subject it is generally administered via an arterial cannula and removed from the subject via a venous canula and discarded or stored.

The solution according to the invention may be used in a variety of surgical settings and procedures. It may be useful in delicate neurosurgery where clear surgical fields are imperative and reduced central nervous system activity may be desirable and achieved by performing the procedure on a patient whose core temperature and or cerebral temperature has been substantially reduced.

The solution according to the invention may be used to maintain a subject at normal body temperatures in a pressurized environment at increased oxygen concentration above atmospheric oxygen tension up to 100% oxygen, until enough blood components can be synthesized by the subject to support life at atmospheric pressure and oxygen concentration. The solution according to the invention may be used to maintain a subject at temperatures lower than normal body temperature and at a reduced rate of metabolism after traumatic life threatening injury until appropriate supportive or corrective surgical procedures can be performed. In addition the solution may be used to maintain a patient having a rare blood or tissue type until an appropriate matching donor can be found and replacement blood units or other organ can be obtained.

Surprisingly it has been discovered that it is possible to replace substantially all of a mammalian subject's circulating blood with the solution according to the invention and to maintain the subject alive without reinfusing blood into the subject. Substantially all of a mammalian subjects circulating blood is considered to be replaced when the subjects hematocrit drops below 10%. The solution according to the invention can of course be used to maintain a subject having a hematocrit in excess of 10%.

The procedure for replacing substantially all of a mammalian subject's circulating blood may be carried out with the mammalian subject's body temperature being maintained at its substantially normal temperature. In addition the procedure may be carried out with cooling of the subject and reduction of the mammalian subject's body temperature below that of its normal temperature. Such cooling may be accomplished by chilling the subject in an ice bath or ice-salt slurry. The subject may be further cooled by chilling the solution according to the invention prior to perfusing the subject with the solution.

In the procedure according to the invention for replacing substantially all of a mammalian subject's circulating blood it is preferred to place the subject in a hyperbaric chamber and to pressurize the hyperbaric chamber with oxygen at concentrations exceeding 20%, preferably 50% or above up to 100% oxygen. The pressure of the hyperbaric chamber is maintained during most of the procedure in a range between 0.5 pounds per square inch over atmospheric pressure to pressures up to about twice atmospheric pressure.

In the preferred embodiment, the subject is chilled and perfused with the solution according to the invention, using an arterial catheter to deliver the solution according to the invention to the subject's circulatory system and an venous catheter to remove blood and the perfusate from the subject. Substantially all of the subjects circulating blood is removed in this manner as determined by measurement of the hematocrit of the effluent from the venous catheter. The procedure is performed with the subject in a hyperbaric chamber at hyperbaric pressures of about 0.07 to about 2 atmospheres over ambient pressure (0.5–30 pounds per square inch [psi]) with 100% oxygen. When substantially all of the subjects circulating blood is removed, perfusion is stopped, cannulas removed and the surgical wounds are closed. If necessary, the pressure of the hyperbaric chamber may be reduced to atmospheric pressure during wound closure. The subject is subsequently maintained at hyperbaric pressure at high oxygen concentration. The pressure is gradually reduced to a lower pressure but one still hyperbaric. Preferably the pressure is maintained below 10 psi to about 5 psi for a number of hours up to a several days. Subsequently, the pressure is again gradually lowered below 1 psi and preferably to about 0.5 psi and is maintained at this pressure for an additional period of time up to a day or more.

The solution may also be used to maintain the physiological integrity of an organ donor subject immediately after the occurrence of brain death. The subject can be chilled, the subject's blood removed and replaced with circulating solution below 37° C., or while circulating cold solution according to the invention. Through this use of the solution ischemia of vital organs after an organ donor subject has been removed from artificial respiratory support can be minimized. By circulating cold solution according to the invention through the subject's circulatory system at low temperature with or without placing the subject in a hyperbaric oxygen chamber, vital organs can be maintained for longer periods of time thus maximizing the number of organs that can be effectively used from one donor for potential transplant recipients.

In another aspect of the invention, it has been discovered that by using certain adducts, particularly propanediol and high concentrations glucose to augment the solution according to the invention, it may be possible to reduce the temperature of donor organs, and in particular donor hearts, below the freezing point of water (0° C.) and recover them from freezing in a state capable of maintaining coordinated cardiac contraction. Furthermore by using the solution according to the invention with such adducts, it has been possible to reduce the temperature of intact mammalian donor subjects below the freezing point of water (0° C.) and restore them from freezing in a state capable of maintaining coordinated cardiac contraction. Other organ systems are also believed to be maintained in a physiological state capable of maintaining life.

The adducts to the solution include low molecular weight alaphatic polyalcohols. Diols, exemplified by ethylenediol, propanediol, and butanediol are preferred. Of these diols propane diol is particularly preferred. Other polyalcohols that may be suitable as adducts for low temperature, sub-zero ° C. preservation of organ and organ donor subjects are low molecular weight polyethylene glycol. It is preferred in this aspect of the invention that the adduct is added to the solution to a final concentration in a range between about 0.2 Molar to 1 Molar. With respect to propanediol, in particular a range of 0.2M to 0.6M is preferred. A concentration of about 0.4M propanediol is most preferred. 1,2 propanediol is preferred as the adduct to the solution used for low temperature organ and donor preservation according to the invention, although 1,3 propanediol may be used.

The glucose concentration in the solution useful for sub-zero ° C. preservation of organ and organ donor subjects ranges between about 0.6M to about 1.4M. A concentration about 1M glucose is preferred.

Another adduct that is useful in the solution according to the invention for low temperature and sub-zero ° C. preservation of organ and organ donor tissues is trimethylamine oxide (TMAO). TMAO may be added to the solution described immediately above to a final concentration in a range between 0.2M and 7M. The solution according to the invention including including TMAO when perfused into a subject leads to improved biological integrity of the subjects tissues as evidenced by superior anatomical preservation of the tissues.

The following Examples are intended to illustrate the invention and its use, and are not intended by the inventors to be limiting of the invention.

EXAMPLE 1

Preparation of Solution: 10 Liters

1. Thoroughly clean large container (for example Nalgene plastic carboy) with soap and water. This container should be carefully calibrated and marked calibrating the level of each liter of solution in the container. In this example, the carboy is calibrated in one liter increments to 10 liters. Ideally, the carboy should hold 10 to 12 liters if preparing 10 liters of solution. The container is thoroughly rinsed using deionized water before use.

2. To the cleaned and rinsed container add first 80 g/L (or 800 g for 10 liters) of pyrogen-free Dextran 40 which may be obtained from chemical supply houses such as Pharmachem or Pharmacia. Add deionized water bringing the volume up to ⅔ to ⅘ of the final desired volume of solution being prepared. Dissolve the Dextran 40 completely by shaking.

3. One can add the remaining chemicals that comprise the solution in any order dissolving each completely before the addition of the next. The following reagents may be obtained from chemical supply houses; in this example the listed reagents were obtained from Sigma.

| Reagent | g/L | g/10 L |
|---|---|---|
| NaCl | 5.2 | 52 |
| $CaCl_2$ | 0.29 | 2.9 |
| $MgCl_2$ | 0.40 | 4.0 |
| Glucose | 0.9 | 9 |
| Tris | 3.03 | 30.3 |
| Na Gluconate | 6.54 | 65.4 |

4. Next, the solution is brought to pH 7.80 at room temperature by the dropwise addition of 0.25M HCl while shaking and monitoring with a pH meter.

5. The solution is then brought to its final desired volume (i.e. 10 L) by the addition of more deionized water. A superior method for more precise volume adjustment is to use a pre-weighed carboy (dry) and bring the final weight up to 9.98 kg above that weight for 10 liters of solution using a sensitive and accurate scale (assuming water density is 0.998 g/ml). Shake well before filtering.

6. Finally, the solution is pumped through a 0.2 μ filter (Gelman, Whatman, or ideally Pall filter units can be used) into sterile containers or bags.

7. The bottled and capped solution is stored on ice until used.

The solution may then be prepared as a sterile dry powder in containers suitable for preparation of sterile IV solutions after freeze drying under appropriate conditions after step 7.

EXAMPLE 2

Hamster revived after 1 hour of ice-cold blood-substitution

A 41 g female hamster (*Mesocricetus auratus*), approximately 1 month old, was injected i.m. with 0.04 ml of Vetalar, a 100 mg/ml solution of the anesthetic ketamine. The animal was packed in crushed ice and chilled until its rectal temperature was 10° C. The animal was removed from the crushed ice and placed ventral side up on a custom-designed stage positioned so that specific portions of the animal could be observed through a stereo-microscope during surgery. Its limbs were secured, and the animal was instrumented with EKG leads and a rectal telethermometer probe.

An incision was made in the right groin region, and the right femoral vein, and then the right femoral artery, were cannulated using specially designed micro-cannulas filled with the solution described herein in Example 1. After cannulation, 0.02 ml of heparin (1000 U/ml) in the Example I solution was injected into the animal through the venous cannula, which was then capped.

After the right femoral arterial cannulation, the cannula was connected to a luer-tipped segment of sterile plastic tubing which was connected to a stopcock mounted on the surgical stage. The stopcock was connected to another tubing segment which was in turn connected to a wider, thicker, and more compliant tubing segment passed through the head of a roller pump. The end of this wider tubing segment contained a tube for drawing up fluid from a reservoir. This tube for drawing up fluid from a reservoir termed a "pick-up" herein was fashioned from the luer end of an 18 gauge hypodermic needle. This "pick-up" was covered with blood filter material which was secured by a small rubber "O" ring. The "pick-up" was inserted into a reservoir of the solution described in Example 1 hereof contained by a centrifuge tube immersed in crushed ice. 0.06 ml of 1M KCl was added to the solution (15 ml) yielding a molar concentration of about 4 mM KCl. The line was closed using the stopcock to prevent backbleeding into the arterial cannula.

The hamster was surrounded with crushed ice, and chilled to 4° C. Then 0.2 ml of 1M KCl was injected into the stopcock, which was opened to allow the injected solution to flow into the line connecting to the arterial cannula, and from there, into the animal's femoral artery. The hamster's heart arrested. The animal was allowed to cool further, and was perfused through the arterial cannula with 8 ml of solution described in Example 1 containing 4 mM KCl. Effluent, containing most of the hamster's blood, was collected from the venous cannula. After the hematocrit dropped below 5, the roller pump was turned off for 67 minutes.

The hamster was then perfused through the arterial cannula with 8 ml of solution described in Example 1 without KCl, followed by 8 ml of heparinized blood taken from other hamsters by cardiac puncture. An equal amount of effluent was collected from the venous cannula. After the hematocrit exceeded 40%, perfusion with whole blood was ended, and the cannulas removed.

The hamster was warmed with a desk lamp, until it became reactive to stimuli. The cannulas were removed, open blood vessels ligated, and incisions closed. Further rewarming continued. The animal fully recovered, and has continued to live for weeks following the experiment.

EXAMPLE 3

Cardiac Preservation After Sub-zero Storage

A fasted (overnight) female hamster, 40 grams, was injected, i.m., with 0.02 ml of Ketamine anesthetic (100 mg/ml). The hamster was immersed in crushed ice until its body temperature lowered to +14° C. It was then placed on a surgical stage and instrumented with EKG leads and a rectal temperature probe. The carotid artery and jugular vein were exposed surgically while the animal's body temperature was maintained between 10°–14° C. and cannulas were inserted into the artery and vein. The arterial cannula was attached to tubing connected to a peristaltic pump. The tubing was filled with the solution described in Example 1 containing in addition 20 mM KCl. The venous cannula was capped until the animal's body temperature was lowered to 5° C. using crushed ice and a temperature-controlled stage set at −1.0° C.

The animal stopped breathing on its own when its body temperature fell below 10° C. Respiration with 100% $O_2$ was initiated At 5° C. the venous cannula cap was removed and 3 5 ml of the solution described in Example 1 hereof was pumped into the artery at a flow rate of about 0.3 ml/minute. Afterwards, 4.5 ml of a cryoprotective solution composed of the solution described in Example 1 hereof and in addition 4 mM KCl, 1.0M glucose, 4% propanediol (i.e. 1.8 g glucose +0.4 g propanediol per 10 ml solution) was infused. During perfusion, the venous effluent was collected. The animal's temperature was lowered gradually to 0° C. during perfusion. Respiration was discontinued 5 minutes following the onset of perfusion. At this time, more than 30% of the subject's blood volume had been removed. The heart continued beating until it eventually stopped. Following perfusion with the cryoprotective solution described in the preceding paragraph, the animal was placed in a sub-0° C. NaCl slush (0.6M) solution which was placed in a freezer overnight.

The freezer temperature was kept at an average of −5° C. Fifteen minutes after the animal was placed in the freezer, its rectal temperature lowered from 0 to −1.0° C. The animal's rectal temperature 12 hours later was −2.5° C. The animal was then warmed to a temperature of about 2.5° C. in a Quasar commercial kitchen microwave oven using 7 second pulses with the setting on warm. The pulses were generated 1 minute apart. Eighteen pulses were needed to thaw the animal.

The animal was again placed on the surgical stage and instrumented with EKG leads and a rectal telethermometer probe. Three and one half ml of the solution described in Example 1 hereof was perfused into the carotid artery at a flow rate of approximately 0.2 ml/min. The animal's body temperature was maintained below 5° C. The hamster was then perfused with whole blood, and gradually warmed.

After 2 ml of blood had been infused, and the animal's temperature had climbed to 13° C., rhythmic EKG signals were detected. With continued perfusion and warming the amplitude of the signals became greater, and they increased in frequency. After 5.5 ml of blood had been infused, and the animals temperature had reached 25° C., the chest of the animal was opened and its heart was observed to beat continuously.

EXAMPLE 4

Synthetic Solution Substitutes for Blood In A Hyperbaric Chamber

A 40 g hamster, previously fasted overnight, was injected with 0.03 ml Ketamine (100 mg/ml) i.m. The hamster was placed in crushed ice, until its body temperature fell below 15° C. The hamster was removed from crushed ice, and placed ventral side up on a temperature-controlled stage positioned for microsurgery below a stereo-microscope. The hamster's temperature was maintained between 12°–15° C.

Following an incision in the right groin area, the right femoral vein and artery were exposed. The femoral vein was cannulated, 0.1 ml of heparin (1000 u/ml) was injected, and the cannula was capped to prevent bleeding.

The right femoral artery was then cannulated, and the cannula was briefly attached to tubing filled with the solution described in Example 1 hereof. The tubing was threaded through the head of a peristaltic pump. A small volume of the solution (approximately 0.3 ml) was infused to keep the arterial cannula void of blood. Both the venous and arterial cannulas were secured to the animal with surgical suture.

The arterial cannula was capped and the animal was moved onto the stage in a hyperbaric oxygen (HBO) chamber. A temperature probe was inserted into the rectum.

The arterial cannula was attached to tubing which passed through a peristaltic pump and into a reservoir. The tubing and reservoir were filled with the solution described in Example 1 hereof containing 4 mM KCl.

The cap was removed from the venous cannula and the HBO chamber was closed and pressurized. The peristaltic pump was turned on, and the animal perfused with solution, which replaced most of its blood. This blood was allowed to drain from the animal as a venous effluent. The final chamber pressure was 1.5 arm over ambient pressure, which was kept constant. The flow rate of solution into the animal was about 0.3 ml/min. The hamster was maintained between 14°–16° C. using the temperature-controlled stage on which the hamster was positioned in the HBO chamber.

Cardiac activity and breathing was maintained throughout this period during the perfusion. After 15 ml of the solution described in Example 1 containing in addition 4 mM KCl was perfused into the hamster replacing the blood, the chamber was gradually depressurized.

The chamber was then opened, and a hematocrit sample was taken. The hematocrit was 5%. The venous and arterial cannulas were capped and the chamber closed and pressurized to 1.5 atm over ambient pressure.

The animal continued to breathe on its own in the chamber for 4 hours after the removal of its blood. After this time, the chamber was depressurized gradually. Concomitantly, the animal was cooled to 12° C. The chamber was opened and the animal was moved to another surgical stage. Ice was placed on the animal and whole blood was perfused into the animal at a flow rate of 0.2 ml/min, as solution was allowed to drain as venous effluent.

After 1 ml of blood was infused, the ice was removed. The hamster's body temperature was at 4° C. The animal was then permitted to warm gradually as the hematocrit was raised by continuous blood infusion.

Artificial respiration was initiated after 1 ml of blood was put back in. The animal's heart never stopped beating rhythmically. At 21° C., the animals was breathing steadily on its own Artificial respiration was discontinued and warming and blood infusion continued until the animal's temperature reached 25° C. The hematocrit was measured to be 40%. Perfusion was discontinued, the cannulas removed, blood vessels ligated and surgical incisions closed.

One hour following the procedure, the animal was very active and alert. Four hours after the experiment, the animal was eating and drinking. At 24 hours after the completion of the above-described procedure, it appeared completely normal with respect to posture and behavior, and has continued to live for weeks since the experiment.

EXAMPLE 5

A 46 g hamster, approx. 1 month old, was inj. i.m. with 0.02 ml Vetalar, a 100 mg/ml solution of ketamine. The anima was surrounded by crushed ice until its rectal temperature was about 12° C. The animal was then removed from the crushed ice and placed ventral side up on an operating stage designed to keep the animal cold, which is under a stereo-microscope. Its limbs were secured, and the animal was instrumented with EKG leads and a rectal telethermometer probe.

An incision was made in the right groin region. A cannula was placed in the right femoral vein, and 0.02 ml of heparin solution (250 U/ml) was injected into the animal through the cannula which was then capped. Then the right femoral artery was cannulated. The cannula was connected to a luer-tipped segment of plastic tubing, and the tubing was passed through a peristaltic roller pump and into a reservoir containing the solution described in Example 1 above containing 0.05M glucose. At the end of the tubing was inserted an 18 G hypodermic needle to which a mesh blood filter material was secured at the hub by a rubber "O" ring. The pump was turned on and fluid in the reservoir was pumped through the tubing into the femoral artery of the animal. When the animal's temperature fell below 9° C. ventilation (at 20 breaths/minute) was initiated using 100% oxygen. The animal was cooled further to a rectal temperature of 4° C. and 0.1 ml of 0.2M KCl was injected into the 24 G angiocath which was inserted in the femoral vein. This injection arrested the heart and EKG signals ceased. The pump was turned on and the solution described above in this example was perfused into the artery at approximately 0.2 ml/min while venous effluent was collected. During the perfusion the animals temperature dropped to near 1° C. After 4 ml of solution was perfused into the animal, the pump was turned off and the animal was kept surrounded by crushed ice in circulatory arrest for 2 hours. Then the animal was perfused with approximately 7 ml of whole blood (which was collected from other hamster blood donors) while the animal was gradually warmed using a desklamp. During the perfusion venous effluent was collected. The same volume pumped into the artery is collected as venous effluent. At 10° C., after the animal remained in cardiac arrest for 3 hours and 11 minutes, heart beats were first observed upon monitoring EKG signals. Ventilation (6 breaths/minute) of the animal was then initiated using 100% oxygen. As the animal was further warmed and heart beats became stronger and faster this rate was increased to about 15 breaths/ minute. When the animals temperature was above 28° C. the animal began to breath on its own and became responsive. Perfusion was discontinued (the hematocrit reading 44%) and cannulas were removed and surgical wounds closed. This hamster has remained alive in apparently normal health for many weeks since the experiment.

EXAMPLE 6

A fasted (overnight) female hamster, 45 grams, was injected i.m. with 0.03 ml ketamine anesthetic (100 mg/ml). The hamster was immersed in crushed ice until its body temperature lowered to about 14° C. The animal was then placed on a surgical platform and instrumented with EKG leads and a rectal temperature probe. The carotid artery and jugular vein were exposed surgically using a stereo microscope. The animal's body temperature was maintained between 10°–14° C. Cannulas were inserted into the carotid artery and jugular vein. The arterial cannula was connected to tubing which passed through a peristaltic pump into a reservoir containing cryoprotective solution composed of the solution described in Example 1 containing, in addition, 11 mM KCl, 1.0M glucose and 4% propanediol. The venous cannula was initially capped until the animals body temperature was lowered to 5° C. using crushed ice and a temperature regulated platform set near –1.0° C.

The animal stopped breathing on its own as the body temperature fell below 10° C. At this time the animal was ventillated at about 15 breaths per minute with 100% oxygen. When the animals temperature fell to 5° C. the venous cap was removed and the pump was turned on at a flow rate of about 0.20 ml/minute. The animal's heart stopped beating 21 minutes later and ventilation was discontinued 5 minutes after the onset of perfusion. During the perfusion blood was collected as venous effluent. Approximately 4 ml of the cryoprotective solution described above in this Example was infused into the animal. Then the animal was surrounded by a salt-ice slurry whose temperature was –2.0° C. The container that held the slurry and animal was placed inside a temperature bath set at –5.0° C. The animals rectal temperature gradually lowered to –3.4° C. in the morning (18 hours after the animal was put in the cooling bath). The container was removed from the cooling bath. The slurry was frozen solid. It was melted using ice-cold water. Upon removing the "slurry" the animal felt frozen. The animal was then placed in a kitchen microwave oven. The oven was set on warm for 7 seconds. The animal was exposed to about 20, 7 second heating cycles over a 20 minute period. This thawed the animal and raised its rectal temperature to about 2° C.

The animal was again placed on the surgical platform and the animal was infused into the carotid artery with the solution described in Example I. The cryoprotecive solution was collected as venous effluent. About 3 ml of the solution described in Example I was perfused into the animal at a flow rate of 0.15 ml/minute. Blood which was collected from hamster blood doners was then perfused in at the same flow rate. After 2 ml of blood was perfused into the artery of the hamster, the hamster was warmed slowly using a desk lamp. As blood perfusion and warming continued, the animals temperature rose above 15° C. and strong rhythmic EKG signals were recorded. Upon surgical thorocotomy actual heart beats could be observed.

EXAMPLE 7

Synthetic Solutions as a substitute for Blood in a Hyperbaric Oxygen Chamber

A 43 gram female hamster (fasted overnight) was injected, i.m., with 0.02 ml of ketamine (100 mg/ml). The hamster was placed in crushed ice until its body temperature fell to about 14° C. The hamster was then placed ventral side up on a temperature-controlled stage positioned for microsurgery below a stereo-microscope. The hamster's temperature was maintained between 12°–15° C. Following an incision in the right groin area, the right femoral vein and artery were exposed. The femoral vein was cannulated, 0.1 ml of heparin (250 u/ml) was injected, and the cannula was capped to prevent bleeding. The right femoral artery was then cannulated and the cannula was attached to tubing passed through a peristaltic pump and into a reservoir filled with the solution described in Example I. A small volume of the solution (i.e. 0.2 ml) was infused to keep the arterial line void of blood. Both the venous and arterial cannulas are secured to the animal. The arterial cannula was capped and the animal was transferred onto the temperature-regulated stage of a hyperbaric oxygen (HBO) chamber. The animal's temperature measured rectally was maintained between 13°–18° C. The purpose of maintaining the hamster in that temperature range was to keep the animals activity low while assuring the animal was breathing on its own and reflexively responsive to stimuli.

The arterial cannula was connected to tubing that passed outside the chamber through a peristaltic pump and into a reservoir (inside the chamber) which contained the solution described in Example I and 2.5 mM KCl. The cap was removed from the venous cannula and the pump was turned on at a flow rate of about 0.2 ml/min. As The solution was perfused into the animal venous effluent (blood) was collected. The chamber was quickly closed and gradually pressurized to 20–24 psi (100% oxygen). After about 1 hour of perfusion under pressure the chamber was gradually depressurized over a period of about 1 hour. Then perfusion was discontinued. A total of about 13 ml of solution was perfused into the animal. The cannulas were capped after a sample of venous effluent was taken to determine the hematocrit. The animal was placed again on a surgical platform and the cannulas are pulled out and wounds tied. The animal showed some veryminimal reflex activity during this time although the animal has little blood and was breathing room air. The animal is quickly placed in a box inside the chamber which was pressurized gradually to about 20 psi. In the chamber was placed food and water for the hamster. A heat lamp was used to warm the chamber and the animal. The pressure in the chamber was gradually lowered (over a 1 hour period) to 5 psi. The animal's activity increased over the one hour period until it became quite active. The animal was maintained in the chamber for about 16 hours at 5 psi. The pressure was then gradually lowered to 0.5 psi (100% oxygen) and maintained at that pressure 24 hours Then the animal was taken out of the chamber and was placed in a normal cage. The animal has continued to appeared completely normal many weeks following the experiment.

EXAMPLE 8

Use of the Solution Augmented with Potassium Chloride to Blood Substitute Primates In this example an 8 kg. juvenile male baboon of the species Papio anubis was injected i.m. with 60 mg of ketamine. A 22 gauge ×1¼ in. catheter was inserted in the right cephalic vein, and 3 ml of 2.5% pentothal was injected i.v. The ape was then fitted with an endotracheal tube, placed on a surgical table, and ventilated with an 0.7–2.5% mixture of Flether in 100% $O_2$, titrated to the animal's activity. The eyes were coated with lacrylube for protection.

The ventilator was set at 18 breaths per minute (bpm), its stroke volume was 240 ml, and the inspiratory/expiratory ratio was 37%. Airway pressure was maintained at approximately 10 mm Hg, and the volume delivered with each respiration was checked by examining the airway pressure trace on a CRT or strip-chart recorder. Airway pressure was monitored on-line by computer.

The animal was shaved, and Ringer's lactate drip was initiated i.v. a flow rate of 1–3 ml/minute with the rate titrated to the animal's arterial blood pressure. Terramycin was administered.

The extracorporeal circuit consisted of a blood oxygenator, blood reservoir and pump and was constructed with a secondary in-line heat exchanger added as close to the animal as possible. It was further equipped with an external ice water reservoir. The ice-water reservoir had a pump to supply the oxygenator's built-in heat exchanger, as well as the secondary heat exchanger with circulating ice water. All tubing in contact with blood or blood substitute was sterile. The oxygenator reservoir and circuit was filled with 2 liters of the solution described in Example I.

KCl (4 ml of 2.0M) was added to the 2 liters of the solution described in Example I in oxygenator reservoir and bypass circuit, yielding a KCl concentration of 4 mM. A 5F NIH catheter for monitoring arterial pressure was introduced into the left brachial artery. To it was attached a 3-way stop-cock (to allow arterial blood sampling every 10–60 minutes throughout the entire procedure). Blood gases, pH, K+ and hematocrit were measured in each sample, and in some cases, electrolytes, and enzymes as well. The catheter was attached to a pressure transducer. The transducer was connected to a computer to monitor central arterial pressure (CAP). Other temperature and pressure parameters were also measured on-line by the same computer.

A 6F NIH catheter was inserted into a distal branch of the left brachial vein to allow computerized monitoring of central venous pressure (CVP). A thoracotomy was performed and a 6F coronary catheter was inserted into the left atrium to monitor left atrial pressure.

A 10F arterial cannula was placed in the left femoral artery and a 16F venous cannula was placed in the left femoral vein. Methyl prednisolone (80 mg) was introduced i.v. An esophageal tube was inserted, and 3 ml of Maalox was administered. The esophageal tube was fitted with a thermistor probe for recording deep esophageal temperature.

Due to the extensive surgical procedures, the baboon spent about five hours on anesthetic. After the EKG leads were in place, the animal was put in a netted sling and lowered into an insulated ice chest. It was then immersed in crushed ice. After 1 hour and 6 minutes of chilling in crushed ice, body temperature sank to 23° C. Nipride (25 mg sodium nitroprusside in 500 ml of 5% aqueous dextrose) infusion was begun at a rate of 6 ml/hr. The animal was placed on bypass 17 minutes later, when the temperature had declined to 21° C.

At that time, 200 ml of whole blood were removed from the baboon as venous effluent. The clamps were released which isolated the ape's circulation from the bypass circuit, and 2 liters of the solution described in Example I, to which were added 2 ml of 2M KCl (final concentration 2 mM KCL), were allowed to blood-substitute the animal. Following this, its heart was arrested by the i.v. administration of 15 ml of 2M KCl.

A blood-blood-substitute mixture was continuously removed as a venous effluent until 4 liters of the solution described in Example I (to which 22 ml of 2M KCl had been added) replaced the circulating solution. After 50 minutes of chilled blood substitution, the primate's temperature had declined to 3° C. Flow through the animal appeared good and there was little tendency for the pulmonary arterial wedge pressure to elevate along with perfusion of the femoral artery. The cause of this increased flow, and relatively rapid pace of temperature decline may be related to the use of nitroprusside, and also the relatively sparing use of anesthetics during chilling, which resulted in the animal being somewhat more active as it was cooled.

Following blood-substitution, the animal was placed on circulatory standstill for one hour and 40 minutes. At the end of the standstill period, 2 liters of ice-cold solution as decribed in Example I was added to the circuit, replacing 2 liters removed as venous effluent. The minimum body temperature recorded was 2.8° C. Rewarming was then begun. After 13 minutes of warming, the animal's body temperature reached 10° C. and 800 ml of a 1:3 mixture of blood and blood-substitute, followed by 450 ml of a 1:1 mixture, and finally, approximately 1 liter of whole blood was added to the circuit, replacing the solution described in Example I .

Immediately after blood was introduced into the animal, heartbeat was detected. Over the next hour and 22 minutes, 40 ml of $NaHCO_3$, were introduce iv. Mechanical ventilation was begun, and a dopamine drip (200 mg in 250 ml) was administered at 30 ml/hr. $CaCl_2$ (50 mg) was also injected iv. Approximately one hour later, when the body temperature climbed to near normal, the animal was taken off bypass and the ape was placed on a whole blood drip. The animal's blood gases and blood pressures stabilized in the normal range.

One hour later, the cannulas were removed., Since the animal had been catheterized following a thoracotomy, it was decided that the long term post surgical management of the animal would not be attempted, due to the behavioral problems of restraining an untamed baboon while treating potential chest infections. When ventillation was discontinued. after another hour, the animal displayed agonal movements and went into cardiac arrest. As the ape's blood pressures and blood gasses had stabilized it is clear that the animal had the potential to survive after being blood-substituted below 10° C. (deep esophageal temperature) for 2 hours and 30 minutes.

EXAMPLE 9

Use of Solution Without Augmentation in Blood Substitution of Primates

Summary

In this example an 8 kg. juvenile male baboon of the species *Papio anubis* was chilled and blood-substituted below 10° C. for 1 hour and 22 minutes. Prior to chilling and blood replacement, a 4F 60 cm Swan-Ganz arrow wedge catheter was placed in the pulmonary artery via the right femoral vein. This permitted measurement of the pulmonary arterial wedge pressure without performing a thoracotomy.

Keeping the animal anesthetically light, and using nitroprusside when the temperature fell to 28° C., improved flow through the bypass circuit. Although the entire procedure went smoothly, an iv injection of 50 mg calcium chloride after citrated blood was introduced during warming caused massive clot formation and termination of the experiment. At that time there was no heparin in the cardiovascular system.

Procedure

The baboon was injected i.m. with 70 mg of ketamine. A 22 gauge×1¼ in. catheter was inserted in the left cephalic vein, and 3 ml of 2.5% pentothal was injected i.v. The ape was then fitted with an endotracheal tube and moved to the x-ray room. It was placed on an x-ray table, and ventilated with a 1% mixture of isoflourane (Flether) in 100% $O_2$, and a 4F 60 cm arrow wedge catheter was implanted in the pulmonary artery through the right femoral vein.

The ventilator was set at 20 bpm, its stroke volume was 200 ml, and the inspiratory/expiratory ratio was 37%. Airway pressure was maintained at approximately 10 mm Hg, and the volume delivered with each respiration was checked by examining the airway pressure trace on a CRT or strip-chart recorder. Airway pressure was monitored on-line by computer.

The animal was shaved, and a 1–3 ml/minute Ringer's lactate drip was initiated i.v., with its rate titrated to the animal's arterial blood pressure.

The extracorporeal circuit was as described in the previous Example. The oxygenator reservoir and circuit was filled with 2 liters of the solution described in Example I.

A 20 guage hydromere catheter was placed in the right femoral vein to allow computerized monitoring of central venous pressure (CVP). A 3-way stopcock was placed in-line to allow sampling. A 20 gauge hydromere catheter for monitoring arterial pressure was introduced into the right brachial artery. To it was attached a 3-way stop-cock (to allow arterial blood sampling every 10–60 minutes throughout the entire procedure). Blood gases, pH, K+ and hematocrit were measured in each sample, and in some cases, electrolytes, and enzymes as well. The catheter was attached to a pressure transducer. The transducer was connected to a computer to monitor central arterial pressure (CAP). Other temperature and pressure parameters were also measured on-line by the same computer.

A 14F venous cannula was placed in the left femoral vein and a 10F arterial cannula was placed in the left femoral artery. After the venous cannula was implanted, 2.6 ml of heparin was injected iv. An esophageal tube was inserted, and 3 ml of Maalox was administered. The esophageal tube was fitted with a thermistor probe for recording deep esophageal temperature. Methyl prednisolone (80 mg) was introduced i.v. The eyes were coated with lacrylube for protection. As the animal was anesthetically light, 1 ml of pentothal was administered iv.

The EKG leads were in place, the animal was put in a netted sling and lowered into an insulated ice chest. It was then immersed in crushed ice. After 29 minutes of chilling in crushed ice, body temperature sank to 28° C. The animal was kept anesthetically light, Flether being turned off as the temperature dropped below 30° C. Nipride (sodium nitroprusside—25 mg in 500 ml of 5% aqueous dextrose) infusion was begun at a rate of 20 ml/hr and then increased to 40 ml/hr. Over the next next 20 minutes, the Nipride drip was turned on and off sporadically, as the blood pressure and temperature fell. It was finally turned off when the animal was placed on bypass 27 minutes later and the temperature had declined to 23° C. At that time, the clamps were released which isolated the ape's circulation from the bypass circuit, 2 liters of the solution described in Example I were allowed to blood-substitute the animal, and whole and diluted blood were removed as venous effluent, and saved for revival. Following this, its heart was arrested by the i.v. administration of 10 ml of 2M KCl.

A blood-blood-substitute mixture was continuously removed as a venous effluent until 4 liters of the solution described in Example I replaced the circulating solution. After 39 minutes of chilled blood substitution, the primate's temperature had declined below 4° C. Flow through the animal was rapid. The pressure in the pulmonary circulation, which was readily measured, indicated that the circulation was good, and that the wedge pressure catheter was well placed.

After 50 minutes of blood-substitution below 10° C. the minimum body temperature recorded was 2.9° C. Rewarming was then begun, and after 28 minutes of warming, the animal's body temperature reached 10° C., and 750 ml of whole blood were added to the circuit, replacing the solution described in Example I.

Heartbeat was detected 8 minutes after blood was re-infused into the animal. Over the next 30 minutes while the animal warmed, 10 ml of $NaHCO_3$, were introduced iv. and $CaCl_2$ (50 mg) was also injected iv., as was 80 mg of methyl prednisolone. Within a few minutes of adding the $CaCl_2$, massive clot formation was evident. It was thought that the blood, which was anti-coagulated with citrate, clotted as a result of adding $CaCl_2$. The experiment was then discontinued.

In this experiment, the rate of flow of blood substitute through the animal and bypass circuit appeared high, while the left atrial pressure remained acceptably low. The factors which were thought to contribute to this result were the use of nitroprusside, and the maintenance of a light anesthetic state during the cooling process. 1–2 ml of heparin will be added to the blood prior to its re-introduction into, the animal. It is believed that heparinizing the re-introduced blood will eliminate the massive clotting which caused an unexpected end to this experiment.

The invention described above and claimed herein below embodies novel solutions that may be useful in a number of procedures. Those ordinarily skilled in the art may be capable in light of the teaching of the specification and claims to make certain additions or modifications to the invention without departing from the essence of the invention disclosed.

We claim:

1. A method for maintaining a blood-substituted primate, comprising the steps of:

reducing the subject's temperature to a temperature below normal and above −2.5° C.;

arresting the subject's heart beat;

maintaining the subject in a reduced temperature state from which the subject can be revived by circulating into the cooled subject with arrested heart a single solution consisting essentially of a polysaccharide oncotic agent, a physiologically compatible buffer providing a buffering capacity in a pH range of between about 7.2 to about 7.9, a simple hexose sugar, dissolved chloride salts of calcium, sodium and magnesium, and sodium gluconate, wherein the solution does not contain potassium ions or potassium salt and further wherein the solution has an osmolarity about that of physiologically normal plasma; and reinfusing the subject with warm blood while warming the subject to a point where the subject is revised.

2. The method of claim 1, wherein the simple hexose sugar is selected from the group consisting of glucose, fructose and galactose.

3. The method of claim 1, wherein the physiologically compatible buffer is selected from the group consisting of Tris, HEPES, MOPS, THAM and EPPS buffers.

4. The method of claim 1, wherein the polysaccharide is dextran.

5. The method of claim 4, wherein the dextran has an average molecular weight of in a range from about 30,000 to 70,000 Daltons.

6. The method of claim 5, wherein the dextran has an average molecular weight of about 40,000 daltons.

7. The method of claim 6, wherein the dextran comprises about 8% of said solution on a weight/volume basis.

8. The method of claim 1, wherein the concentration of calcium, sodium and magnesium ion obtained from the dissolved chloride salts of calcium, sodium and magnesium and dissolved organic salt of sodium is within the range of normal physiological concentrations of said ions in plasma.

9. The method of claim 1, wherein the concentration of sodium chloride is in a range from 70 mM to about 160 mM, the concentration of calcium chloride is in a range of about 0.5 mM to 4.0 mM and the concentration of magnesium chloride is in a range of 0 to 10 mM.

10. The method of claim 9, wherein the concentration of sodium chloride is in a range of about 85 to 95 mM.

11. The method of claim 9, wherein the concentration of sodium chloride is about 90 mM.

12. The method of claim 9, wherein the concentration of calcium chloride is in a range of about 1.5 mM to 3.5 mM.

13. The method of claim 9, wherein the concentration of calcium chloride is about 2 mM.

14. The method of claim 9, wherein the concentration of magnesium chloride is in a range of about 1 mM to 10 mM.

15. The method of claim 9, wherein the concentration of magnesium chloride is about 2 mM.

16. The method of claim 1, wherein the concentration of sodium ion obtained from the organic salt of sodium and sodium chloride is sufficient to bring the concentration of sodium ions in the solution to a concentration about that of physiologically normal plasma.

17. The method of claim 1, wherein the organic salt of sodium is sodium gluconate in a concentration range of about 5 mM to 70 mM.

18. The method of claim 63, wherein the concentration of sodium gluconate is about 27 mM.

19. The method of claim 1, wherein said physiologically compatible buffer has a pKa of 7.77 at 37° C. and a Δ pKa/0° C. of −0.031.

20. The method of claim 1, wherein the concentration of Tris is about 25 mM.

21. The method of claim 1, wherein the pH thereof is about 7.8 at about 25° C.

22. The method of claim 1, wherein the osmolarity thereof is about that of physiologically normal plasma.

23. The method of claim 1, wherein the molarity thereof is in a range of 290 mM to about 330 mM.

24. The method of claim 1, wherein the molarity thereof is about 298 mM.

25. The method of claim 2, wherein the concentration of hexose sugar is in a range of about 2 mM to 200 mM.

26. The method of claim 1, wherein the temperature of the subject is reduced to at least 0° C. prior to reinfusing the subject with warm blood and after the solution has been circulating into the subject.

27. The method of claim 1, wherein the subject's heart beat is arrested by administering a cardioplegia agent.

28. The method of claim 1, wherein the subject's heart beat is arrested by the reduction in temperature.

29. A method of maintaining a blood-subStituted primate, comprising the steps of:

reducing the subject's temperature to a temperature below normal and above −2.5° C.;

arresting the subject's heart beat;

maintaining the subject in a reduced temperature state from which the subject can be revived by circulating into the cooled subject with arrested heart a single solution of physiologically compatible components; and reinfusing the subject with warm blood while warming the subject to a point where the subject is revived;

wherein the improvement comprises maintaining the subject with a single solution wherein the level of potassium ions in the solution is below a normal physiological potassium ion level for the subject.

30. The method of claim 29, wherein the improvement comprises maintaining the subject with a single solution which contains no potassium ions.

31. The method of claim 29, wherein the subject is maintained at a temperature in the range of 5° C. to −2.5° C. for a period of time in the range of about 1 hour to about 18 hours.

32. A method for ensuring the revival of a blood-substituted primate maintained at below normal temperatures, comprising the steps of:

reducing the primate's temperature to a temperature below normal and above −2.5° C.;

arresting the primates's heart beat;

maintaining the primate in a reduced temperature state from which the subject can be revived by circulating into the cooled subject with arrested heart a single solution consisting essentially of a polysaccharide oncotic agent, a physiologically compatible buffer providing a buffering capacity in a pH range of between about 7.2 to about 7.9, a simple hexose sugar, dissolved chloride salts of calcium, sodium and magnesium, and sodium gluconate, wherein the solution does not contain potassium ions or potassium salt and further wherein the solution has an osmolarity about that of physiologically normal plasma; and reinfusing the primate with warm blood while warming the subject to a point where the subject is revived.

33. A method for performing surgery on a blood-substituted primate at below normal temperatures, comprising the steps of:

reducing the primate's temperature to a temperature below normal and above −2.5° C.;

arresting the primates's heart beat;

maintaining the primate in a reduced temperature state from which the subject can be revived by circulating into the cooled subject with arrested heart a single solution consisting essentially of a polysaccharide oncotic agent, a physiologically compatible buffer providing a buffering capacity in a pH range of between about 7.2 to about 7.9, a simple hexose sugar, dissolved chloride salts of calcium, sodium and magnesium, and sodium gluconate, wherein the solution does not contain potassium ions or potassium salt and further wherein the solution has an osmolarity about that of physiologically normal plasma; and reinfusing the primate with warm blood while warming the subject to a point where the subject is revived.

* * * * *